United States Patent
Hotta et al.

(10) Patent No.: US 9,782,518 B2
(45) Date of Patent: Oct. 10, 2017

(54) METHOD FOR PRODUCING IMPLANT MATERIAL

(75) Inventors: Yuji Hotta, Okayama (JP); Masataka Sakane, Ibaraki (JP)

(73) Assignees: KURARAY CO., LTD., Kurashiki-shi (JP); University of Tsukuba, Tsukuba-shi (JP)

( * ) Notice: Subject to any disclaimer, the term of this patent is extended or adjusted under 35 U.S.C. 154(b) by 379 days.

(21) Appl. No.: 13/989,606

(22) PCT Filed: Nov. 10, 2011

(86) PCT No.: PCT/JP2011/075973
§ 371 (c)(1),
(2), (4) Date: May 24, 2013

(87) PCT Pub. No.: WO2012/070400
PCT Pub. Date: May 31, 2012

(65) Prior Publication Data
US 2013/0253657 A1    Sep. 26, 2013

(30) Foreign Application Priority Data
Nov. 25, 2010    (JP) ................................. 2010-262538

(51) Int. Cl.
| | |
|---|---|
| *A61L 27/56* | (2006.01) |
| *A61L 27/10* | (2006.01) |
| *A61L 27/36* | (2006.01) |
| *A61L 27/38* | (2006.01) |
| *A61L 27/54* | (2006.01) |

(52) U.S. Cl.
CPC .............. *A61L 27/56* (2013.01); *A61L 27/10* (2013.01); *A61L 27/3616* (2013.01); *A61L 27/3804* (2013.01); *A61L 27/54* (2013.01); *A61L 2300/64* (2013.01); *A61L 2430/02* (2013.01); *A61L 2430/06* (2013.01)

(58) Field of Classification Search
CPC ....................................................... A61L 27/56
See application file for complete search history.

(56) References Cited

U.S. PATENT DOCUMENTS

| | | | |
|---|---|---|---|
| 6,200,606 B1 | 3/2001 | Peterson et al. | |
| 8,524,128 B2 * | 9/2013 | Kuwayama et al. | ... A61L 27/10 264/28 |
| 2004/0057939 A1 * | 3/2004 | Hakamazuka et al. | ........................... A61L 27/3821 424/93.7 |
| 2005/0130301 A1 | 6/2005 | McKay et al. | |
| 2006/0278588 A1 * | 12/2006 | Woodell-May | ......... B01L 3/502 210/787 |
| 2010/0112330 A1 | 5/2010 | Kuwayama et al. | |

FOREIGN PATENT DOCUMENTS

| | | |
|---|---|---|
| CN | 1501818 A | 6/2004 |
| CN | 1565644 A | 1/2005 |
| EP | 2 039 668 A1 | 3/2009 |
| EP | 2039668 A1 * | 3/2009 |
| JP | 2002 282285 | 10/2002 |
| JP | 2003 517259 | 5/2003 |
| JP | 2005 40060 | 2/2005 |
| JP | 2007 527221 | 9/2007 |
| JP | 2010 18459 | 1/2010 |
| WO | WO 99/59500 A2 | 11/1999 |
| WO | WO 9959500 A2 * | 11/1999 |
| WO | 2008 111432 | 9/2008 |
| WO | WO 2008111432 A1 * | 9/2008 ............. A61L 27/10 |

OTHER PUBLICATIONS

Hester, Jeane et al. Principles of Blood Separation and Component Extraction in a Disposable Continuous-flow Single Stage Channel. Blood, vol. 54, No. 1. 1979. pp. 254-268.*
Hester (Principles of Blood Separation and Component Extraction in a Disposable Continuous-flow Single Stage Channel, 1979.*
International Search Report issued Feb. 21, 2012 in PCT/JP11/075973 filed Nov. 10, 2011.

* cited by examiner

*Primary Examiner* — Scott Long
*Assistant Examiner* — Nghi Nguyen
(74) *Attorney, Agent, or Firm* — Oblon, McClelland, Maier & Neustadt, L.L.P.

(57) ABSTRACT

A method for producing an implant material by: (A): setting a porous ceramic material having substantially unidirectionally arrayed pores at any depth position inside a container, (B): filling the container with a cell-containing liquid containing at least bone marrow blood and/or peripheral blood, and (C): applying, on the container, a centrifugal force in the direction along the axis of the container.

4 Claims, 3 Drawing Sheets

(A) 
(B)

(A) 
(B)

(A) 
(B)

METHOD FOR PRODUCING IMPLANT MATERIAL

CROSS REFERENCE TO RELATED APPLICATIONS

The present application is a 35 U.S.C. §371 national stage patent application of International patent application PCT/JP2011/075973, filed on Nov. 10, 2011, published as WO/2012/070400 on May 31, 2012, the text of which is incorporated by reference, and claims the benefit of the filing date of Japanese application no. 2010-262538, filed on Nov. 25, 2010, the text of which is also incorporated by reference.

TECHNICAL FIELD

The present invention relates to a production method of an implant material, a tool to be used for the method and an implant material produced by said method.

BACKGROUND ART

Among the ceramic materials, calcium phosphate-based ceramic material is a main component of bone and tooth, has superior biocompatibility, and is superior in the safety. Therefore, it is widely utilized and studied as a biomaterial such as a medical or dental implant material to be implanted in the living body such as artificial bone, artificial dental root and the like, scaffold for cell culture to be used for regenerative medicine and the like, a drug carrier for drug delivery system (DDS) and the like.

However, when a bone defect is large, it is difficult to repair the bone with a single ceramic material. In addition, it is difficult to repair cartilaginous parts having a lower repair function than bone.

With such background, the development of an implant material, wherein cells having a tissue repair capacity such as bone marrow-derived mesenchymal stem cells and the like are seeded on a porous ceramic material, is ongoing.

In such implant material, when bone marrow-derived cells having a tissue repair capacity are seeded on a porous ceramic material, it is desirable to remove red blood cells unnecessary for tissue regeneration from the bone marrow blood, and seed only the useful cells such as stem cells and the like in a concentrated state.

As a production method of an implant material seeded with cells, (1) a method of adding dropwise a liquid containing cultured cells, (2) a method of immersing a porous body in a liquid containing cells, (3) a method of loading a pressure with a piston and the like on an airtight container containing a liquid containing cells and a porous body, (4) a method of loading a centrifugal force on a container containing a liquid containing cultured cells and a porous body, and the like are known.

For example, patent documents 1-4 describe seeding methods using a centrifugal force. In 1 and 4, cells collected from the patient and cultured was seeded and, in 2 and 3, all the cells were seeded on a material, where the cell distribution state in a liquid cannot be controlled.

In patent document 5, a method including placing a porous body in coexistence with a liquid in a container, sliding a piston on the inner face of the container to allow penetration of the liquid into the porous body in advance, and seeding the cultured cells is disclosed. However, even this method cannot control the distribution state of the cells.

Therefore, it is difficult by a conventionally-known method to selectively seed cells in a liquid, which are in a concentration state.

DOCUMENT LIST

Patent Documents patent document 1: JP-A-2002-282285
patent document 2: JP-A-2003-319953
patent document 3: JP-A-2005-137478
patent document 4: JP-A-2005-40060
patent document 5: JP-A-2006-25635

SUMMARY OF THE INVENTION

Problems to be Solved by the Invention

The present invention has been made in view of the above-mentioned situation, and the problem to be solved thereby is provision of a method of producing an implant material, comprising seeding useful cells on a porous ceramic material while controlling the distribution state of useful cells in a cell-containing liquid such as bone marrow blood, peripheral blood and the like (particularly useful cells in the cell-containing liquid in a concentrated state) to rapidly introduce a tissue (particularly bone tissue or cartilage tissue) into the porous ceramic material, without collecting and cultivating the useful cell in advance, and a tool for producing an implant material to perform the method, and a kit for producing the implant material.

Means of Solving the Problems

To solve the above-mentioned problems, the present invention adopts the following constitution.

[1] A method of producing an implant material, comprising
  step (A): a step of setting a porous ceramic material having substantially unidirectionally arrayed pores at any depth position inside a container,
  step (B): a step of filling the container with a cell-containing liquid containing at least bone marrow blood and/or peripheral blood, and
  step (C): a step of applying, on the container, a centrifugal force in the direction along the axis of the container.
[2] The production method of the above-mentioned [1], wherein, in step (A), the porous ceramic material is set such that the long axis of the substantially unidirectionally arrayed pores is along the axis of the container.
[3] The production method of the above-mentioned [1] or [2], wherein the centrifugal force is controlled to 100×g-2000×g in step (C).
[4] The production method of the above-mentioned [1] or [2], wherein the cell-containing liquid is centrifuged to form a buffy coat layer in step (C).
[5] The production method of the above-mentioned [4], wherein, in step (A), the porous ceramic material is set such that at least a part thereof comes into contact with the buffy coat layer produced in step (C).
[6] An implant material obtained by the production method of any of the above-mentioned [1] to [5].
[7] A tool for producing an implant material, comprising
  a container capable of accommodating a cell-containing liquid containing at least bone marrow blood and/or peripheral blood, and a porous ceramic material, and
  a porous ceramic material positioning means having through holes permitting the cells in the aforementioned cell-containing liquid to pass through, which is for setting the aforementioned porous ceramic material at any depth position inside the aforementioned container.

[8] A kit for producing an implant material, comprising
a porous ceramic material,
a container capable of accommodating a cell-containing liquid containing at least bone marrow blood and/or peripheral blood, and the aforementioned porous ceramic material, and
a porous ceramic material positioning means having through holes permitting the cells in the aforementioned cell-containing liquid to pass through, which is for setting the aforementioned porous ceramic material at any depth position inside the aforementioned container.

[9] The kit of the above-mentioned [8], wherein the porous ceramic material is a porous ceramic material having substantially unidirectionally arrayed pores.

Effect of the Invention

According to the present invention, since cells useful for bone tissue formation or cartilage tissue formation can be concentrated and seeded inside a porous ceramic material, an implant material particularly suitable as an osteochondral filling material and the like can be produced conveniently and efficiently.

DESCRIPTION OF EMBODIMENTS

Figure 1:
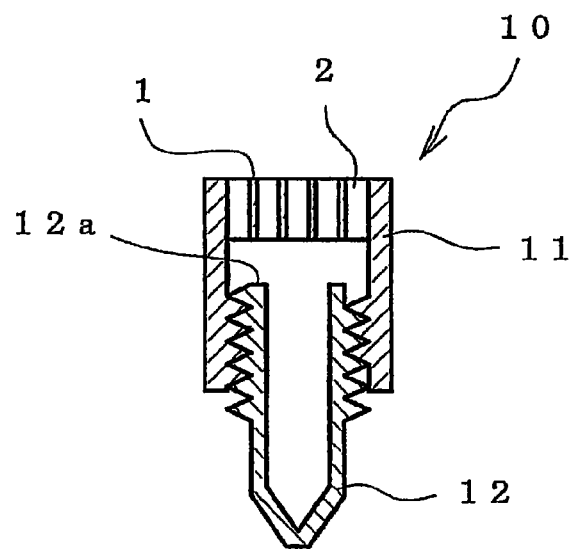
FIG. 1 is a schematic view of one embodiment of a porous ceramic material positioning means for setting a porous ceramic material at any depth position inside a container, which is used for the production method of the implant material of the present invention.

The present invention is explained in the following by referring to its embodiment.

The porous ceramic material to be used in the present invention is preferably a porous calcium phosphate-based ceramic material.

Examples of calcium phosphate-based ceramics include hydroxyapatite, fluorapatite, chlorapatite, tricalcium phosphate, calcium metaphosphate, tetracalcium phosphate, calcium hydrogen phosphate, calcium hydrogen phosphate dihydrate and the like. A mixture of any two or more selected from these can also be used. In addition, in the material of the present invention, a part of Ca component of the calcium phosphate may be substituted by one or more kinds selected from Sr, Ba, Mg, Fe, Al, Y, La, Li, Na, K, Ag, Pd, Zn, Pb, Cd, H and other rare earth elements. In addition, a part of ($PO_4$) component may be substituted by one or more kinds selected from $VO_4$, $BO_3$, $SO_4$, $CO_3$, $SiO_4$ and the like. Furthermore, a part of (OH) component may be substituted by one or more kinds selected from F, Cl, O, $CO_3$, I and Br.

For bone formation, the calcium phosphate is preferably selected from hydroxyapatite, fluorapatite, chlorapatite and tricalcium phosphate, more preferably hydroxyapatite and/or tricalcium phosphate.

The porous ceramic material to be used in the present invention has a porosity of preferably 40-90%, more preferably 50-90%, further preferably 60-90%. When the porosity is not less than 40%, many cells penetrate into and are adhered to the material, which is expected to result in the formation of a sufficient tissue, for example, a bone tissue. On the other hand, when the porosity is not more than 90%, the material is sufficient for general handling and is not broken by a centrifugation operation.

The porosity is calculated according to JIS R 1634. To be specific, a cylindrical test piece with diameter 6 mm×height 8 mm is cut out from a porous ceramic material to be evaluated. The weight and volume of the test piece are measured and the porosity is calculated by the following formula.

bulk density=(weight of test piece)/(volume of test piece)

porosity=(1−bulk density/theoretical density)×100

The porous ceramic material to be used in the present invention has pores which are arrayed substantially unidirectionally. The "pores being arrayed substantially unidirectionally" means that plural pores extending in the uniaxial direction are present and, for example, not less than half, preferably not less than 80%, of such pores have the long axis direction with an angle of not more than 30°. The "angle" here means an intersectional angle shown by orthogonal projection of the long axis of respective pores on any flat plane. Since the porous ceramic material has substantially unidirectionally arrayed pores, it has cell-containing liquid permeability, which allows a cell-containing liquid such as blood, bone marrow fluid and the like to pass through the inside of the material by going through the pores. The "cell-containing liquid going through the pores" here means that a liquid component (tissue fluid) and cells in the cell-containing liquid pass through.

The cross-sectional area of each pore in the ceramic material (that is, the sectional area perpendicular to the long axis of the pore) is preferably $0.05 \times 10^{-3}$-$100 \times 10^{-3}$ mm$^2$, more preferably $0.05 \times 10^{-3}$-$50 \times 10^{-3}$ mm$^2$. A size within the above-mentioned range is sufficient for blood and bone marrow fluid to pass through, and causes a capillary phenomenon that allows easy passage of a tissue fluid such as blood, bone marrow fluid and the like. To solve the problems of the present invention, however, it is not entirely necessary to ensure the above-mentioned cross-sectional area of every pore inside the material.

The porous ceramic material to be used in the present invention can be produced by a known method. Specific examples include a method of forming pores in a ceramics slurry by a foaming agent, a method of forming pores by mixing a substance that carbonizes on firing and eliminating the substance as a gas such as $CO_2$ and the like in a sintering process, a method of using an ice sublimation mark, which is produced during coagulation of a slurry, as a pore and the like. The porous ceramic material having substantially unidirectionally arrayed pores, which is preferable as the porous ceramic material of the present invention, can be obtained by unidirectionally freezing a ceramic slurry to form needle-like ice grown unidirectionally, and sublimating the ice, followed by firing.

Figure 2:
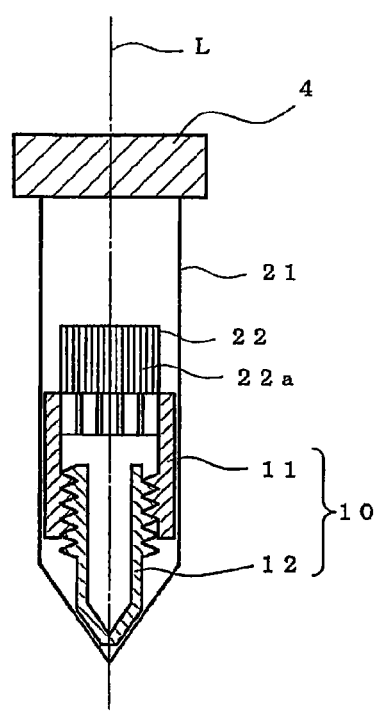
FIG. 2 is a schematic view of a porous ceramic material set at any depth position inside a container by using the positioning means of FIG. 1.

FIG. 1 is a schematic view of one embodiment of a porous ceramic material positioning means for setting a porous ceramic material at any depth position inside a container (hereinafter to be also simply abbreviated as "positioning means") and FIG. 2 is a schematic view of a porous ceramic material set at any depth position inside a container by using the positioning means of FIG. 1.

A porous ceramic material positioning means 10 consists of a stopper 11 and an adapter 12, and has a structure wherein the fixed stopper 11 is attached like a cap on the adapter 12. The stopper 11 is a tube having a top board on one side thereof in the axis-edge direction, and the adapter 12 is a member for adjusting the height position of the top board 1 of the stopper 11 in conjunction with the stopper 11. The surface of the top board 1 of the stopper 11 is a surface on which a porous ceramic material 22 is placed.

Plural through holes 2 permitting the cells to pass through are formed in the top board 1 of the stopper 11, and the cells can freely move to the bottom (that is, adapter 12 side) by passing through holes 2. The sectional size of the through holes 2 (that is, the section orthogonal to the long axis of the through hole) only needs to allow the cells to pass through. Also, the sectional shape of the through hole is not particularly limited and when, for example, the section of the through hole is a circle, the pore size (diameter) thereof is preferably not less than 0.5 mm, more preferably not less than 1.5 mm, from the aspect of cell permeability. The pore size is preferably not more than 6 mm, more preferably not more than 4 mm, to disperse and support the centrifugal force acting on the top board. Furthermore, the size of every through holes does not need to be uniform, and a small-sized through hole may be disposed in the clearance between large-sized through holes in an attempt to increase the proportion (area ratio) of the through hole in the section of the top board (i.e., the section orthogonal to the thickness direction of the top board). When a through hole has a sectional shape other than a circle, the size of the section of the through hole preferably corresponds to the area of a circle having a diameter within the above-mentioned range.

When the proportion (area ratio) of the through hole 2 in the section of the top board 1 of the stopper 11 is too high, the strength of the top board tends to decrease and, when it is too small, the passing of the cells tends to be prevented. Therefore, the area ratio ([total sectional area of through holes present in the section of top board/sectional area of top board]×100) is preferably about 50-95%, more preferably about 60-90%. While the thickness of the top board is not particularly limited, it is preferably about 1-7 mm, since a top board which is too thin tends to show a weak strength and a top board which is too thick reduces the movement range for positioning.

Adapter 12 is used to dispose the top board 1 of the stopper 11 at an intermediate position in the depth direction of a container 21, and movably support the top board 11 in the depth direction of the container 21.

Stopper 11 and adapter 12 are connected in a manner that permits change of the height of the top board 1 of the stopper 11 relative to the adapter 12 (i.e., separation distance between the upper end of adapter 12 and top board 1).

While the means for changing the height of the top board 1 of the stopper 11 relative to the adapter 12 is not particularly limited and various means can be used, a screw mechanism is preferable in view of easiness of operation, simplicity of the structure (easy processing) and the like. Positioning means 10 in FIG. 1 is constituted with the stopper 11 and the adapter 12 connected by such screw mechanism, wherein the inside wall of the stopper 11 and the outside wall of the adapter 12 are screwed together.

It is important that the porous ceramic material-positioning means 10 (stopper 11 and adapter 12) in the present invention have resistance to sterilization and strength standing the centrifugal force. For example, it is preferably formed with a metal such as stainless steel and the like, or a resin such as PEEK (polyetheretherketone) and the like.

When an implant material is produced in the present invention, a porous ceramic material is first set at any depth position inside a container (step A). That is, in step (A), the porous ceramic material positioning means 10 (stopper 11 and adapter 12) is inserted inside a container 21 and a porous ceramic material 22 is placed on the top board 1 of the stopper 11. By setting the height of the top board 1 of the stopper 11 relative to the adapter 12 to a desired level in advance, the porous ceramic material 22 can be set at any depth position inside the container 21 (FIG. 2).

Since the container 21 is filled with, as mentioned below, a cell-containing liquid such as bone marrow blood, peripheral blood and the like, it is important to form the container from a transparent material so that the cell distribution state in the cell-containing liquid can be visually observed. For example, it is preferably formed from a resin such as polypropylene, polystyrene, acrylic resin and the like, glass and the like.

While the shape of the container 21 is not particularly limited, a centrifugal force is applied on the container 21 in a centrifuge as mentioned below. Thus, a cylindrically-shaped container is preferably used to facilitate setting in a centrifuge. Moreover, since a porous ceramic material positioning means 10, wherein the height of the top board 1 of the stopper 11 relative to the adapter 12 changes, is inserted into the inside of the container 21 as mentioned above, the part in the container 21, which corresponds to at least the movable range of the stopper 11, preferably has the same shape and size of the cross section.

The cell-containing liquid to be used in the present invention basically includes bone marrow blood and/or peripheral blood. The bone marrow blood and peripheral blood used are those derived from human or animal (particularly mammal).

Furthermore, the cell-containing liquid may be a mixture of the peripheral blood and/or bone marrow blood and other new cells or other cell-containing liquid. Examples of the cell sauce to be newly added include cord blood; stem cells collected from bone marrow blood, peripheral blood, fat, cord blood, embryo, cancellous bone, periosteum and the like; differentiated stem cells and the like. In addition, an anticoagulant such as heparin, citric acid and the like can also be added to the cell-containing liquid to prevent coagulation of fibrin.

As mentioned above, the porous ceramic material 22 to be used in the present invention has substantially unidirectionally arrayed pores. As shown in FIG. 2, the porous ceramic material 22 is placed such that the long axis of the substantially unidirectionally arrayed pores 22a is along axis L of the container 21, whereby the cells in the cell-containing liquid filled in the container 21 pass through the pores by the action of centrifugal force in the below-mentioned step (C). The "long axis of substantially unidirectionally arrayed pores 22a is along axis L of the container" means that the intersection angle of the major axis of not less than half (preferably 60% or more, more preferably 70% or more) of the substantially unidirectionally arrayed pores and the axis of the container (intersection angle of the orthogonal projection of the major axis of the pores and the axis of the container on any flat plane) is within 30°, where a smaller possible intersection angle is more preferable.

In step (B), a cell-containing liquid is filled in the container 21 obtained in step (A), wherein the porous ceramic material 22 is set at any depth position inside the container. The insertion opening (entrance) of the container 21 is installed with, for example, a removable cap 4 made of polyethylene and the like to tightly seal the container 21, so that entry of foreign substances such as dust and the like into the container can be prevented during transfer from step (A) to step (B) and/or from step (B) to step (C) described below and the like.

In step (C), a centrifugal force is applied to the container 21 filled with the cell-containing liquid and sealed with cap 4, which was obtained in step (B). The centrifugal force can be applied using a general centrifugal separator (centrifugal force applying means), wherein the rotating part of the centrifugal separator is rotated to apply, on the container 21, a centrifugal force heading toward the depth direction (that is, centrifugal force in the direction along axis L of the container 21 (arrow F in FIG. 3)). The centrifugal force in this case is preferably 100×g-2000×g, more preferably 100×g-1500×g.

When a cell-containing liquid such as bone marrow blood, peripheral blood and the like is centrifuged with a centrifugal force within the above-mentioned range, the cell-containing liquid is centrifuged to form a buffy coat layer. The buffy coat layer is known to contain concentrates of nucleated cells such as stem cells having an ability to differentiate into bone and cartilage, platelets, cytokines useful for tissue repair, and the like. On the other hand, erythrocytes are scarcely involved in tissue repair of bone and cartilage.

Figure 3:
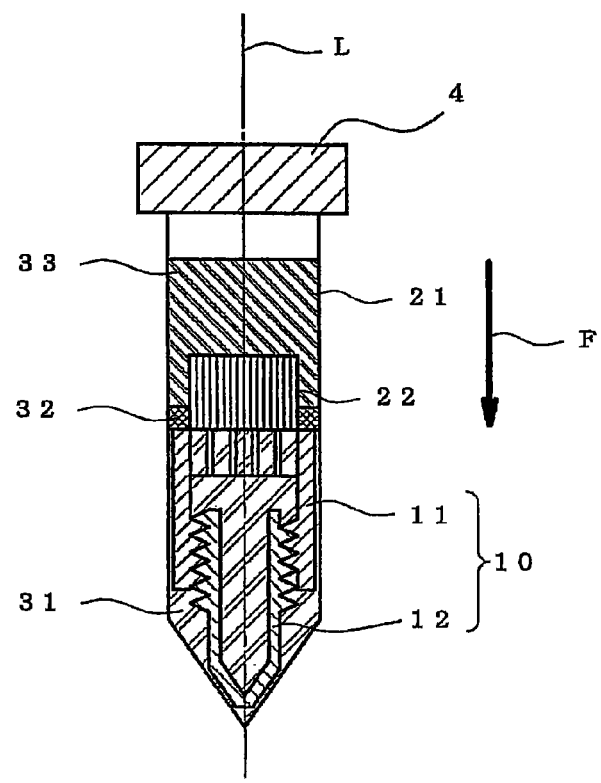
FIG. 3 is a schematic view of a state wherein, in the production method of an implant material of the present invention, a porous ceramic material is set inside a container such that the lower end thereof contacts a buffy coat layer, bone marrow blood and/or peripheral blood is filled therein, and a buffy coat layer is formed by centrifugation.

FIG. 3 is a schematic view showing a preferable condition inside the container 21 after filling a cell-containing liquid such as peripheral blood, bone marrow and the like and centrifuging the container 21 with a centrifugal force within the above-mentioned range. The cell-containing liquid is centrifuged, and an erythrocyte layer 31, a buffy coat layer 32 and a serum layer 33 are formed from the bottom to the upper part of the container 21. While the serum layer 33 does not contain nucleated cells and cytokines at concentrations as high as those of the buffy coat layer 32, it contains proteins, cytokines and the like useful for adhesion, growth and differentiation of the cells.

While the centrifugation time varies depending on the size of the container 21, a cell-containing liquid to be used and the like, it is generally 1-20 min, preferably 5-15 min. When the centrifugation time is shorter than 1 min, the cells and a tissue fluid tend to be insufficiently separated, and when it is longer than 20 min, the damage on the cells tends to increase. The temperature of the cell-containing liquid in the container during centrifugation is preferably 3-6° C.

Since both the porous ceramic material 22 and the positioning means 10 (top board 1 of stopper 11) in the container 21 have pores permitting cells in the cell-containing liquid to pass through (pores 22a, through hole 2), when a centrifugal force is applied to the container 21 filled with a cell-containing liquid, the cell-containing liquid is centrifuged to form a buffy coat layer in the same manner as when a centrifugal force is applied to the container in the absence of the porous ceramic material 22 and the positioning means 10 (container 21 filled only with a cell-containing liquid).

Figure 4:
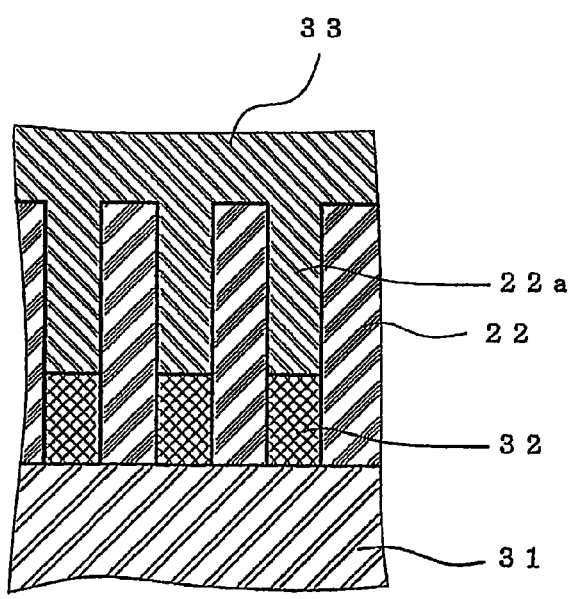
FIG. 4 is a magnified view of the main section of FIG. 3.

FIG. 4 is a magnified view of the main part of FIG. 3. When the depth position of the porous ceramic material 22 in the container 21 (position in depth direction of container) in step (A) is set such that at least a part of the porous ceramic material 22 contacts (overlaps with) a buffy coat layer 32 produced in step (C), the buffy coat layer 32 enters and is encapsulated in the pores 22a of the porous ceramic material 22, as shown in FIG. 4, and a buffy coat component attaches to the inner surface of the pores 22a of the porous ceramic material 22. The buffy coat component contains concentrates of nucleated cells, cytokines and the like, which function extremely effectively for the regeneration of bone tissue and cartilage tissue. Here, since the buffy coat component is attached to the inner surface of the pores 22a of the porous ceramic material 22, it does not fall off easily from the implant material until implanted in the body. FIG. 4 shows a preferable embodiment of the setting position of the porous ceramic material 22 in the container, wherein the lower end of the porous ceramic material 22 contacts (overlaps with) the buffy coat layer 32, and the rest of the porous ceramic material 22 contacts (overlaps with) a serum layer, so that the component of the serum layer that acts on the regeneration of bone tissue and cartilage tissue also attaches to the porous ceramic material 22. When the porous ceramic material 22 having a thickness equivalent to that of the buffy coat layer 32 is used, a porous ceramic material containing only the concentrates of nucleated cells, cytokines and the like, which are derived from the buffy coat component and attached to the inside thereof, can be obtained. The above-mentioned lower end of the porous ceramic material 22 means the end on the side to be in contact with the positioning means 10 in the porous ceramic material 22.

While the position of the buffy coat layer 32 to be formed in step (C) varies depending on the individual from whom a cell-containing liquid such as bone marrow blood, peripheral blood and the like is collected, it can be clarified in advance by applying a centrifugal force in absence of only the porous ceramic material 22 (i.e., in the state that positioning means 10 is inserted in container 21 and the container is filled with cell-containing liquid).

By performing the above-mentioned steps, an implant material, wherein useful cells in a cell-containing liquid are concentrated and seeded on porous ceramic material 22, is produced.

The thus-obtained implant material of the present invention is useful as a bone graft material, an osteochondral graft material, a material for regenerative medicine and the like.

Furthermore, for the purpose of regenerating a bone tissue and cartilage tissue more efficiently, the implant material of the present invention may be used after an operation to cultivate the seeded cells. In addition, a substance having an action to promote growth of a tissue, for example, bone tissue and cartilage tissue, such as a transforming growth factor (TGF-β), bone morphogenetic protein (BMP) and the like may be impregnated in, adsorbed onto or immobilized onto the implant material of the present invention.

The above-mentioned container 21 capable of accommodating a cell-containing liquid and a porous ceramic material, and the porous ceramic material positioning means 10 constitute the tool for producing an implant material of the present invention. In addition, the kit for producing an implant material of the present invention is constituted by providing the aforementioned porous ceramic material 22 together with such tool for producing an implant material.

EXAMPLES

While the present invention is explained in more detail in the following by referring to Examples, the present invention is not limited by the Examples described below.

[Confirmation of Buffy Coat Position]

In container 21 of a (cylindrical) polypropylene centrifugation tube (inner diameter 14 mm, volume 15 mL, manufactured by Greiner GmbH (Germany)), stopper 11 manufactured by PEEK which the outer diameter of a tube was 13 mm (thickness of top board: 5 mm, through hole: circular through hole having diameter 2 mm, area ratio of through hole: 60%) and cylindrical adapter 12 (inner diameter: 7 mm) connected with said stopper in a screw mechanism were set. Rabbit heart blood was filled to the 8 mL scale of the container and centrifuged at 4° C. and 1500×g for 10 min. The container was taken out after centrifugation, the position of the buffy coat layer was visually confirmed and was at the 5.0 mL-5.1 mL scale of the container.

Example 1

Using a container, a stopper and an adapter same as the container 21, stopper 11 and adapter 12 used in the above-mentioned confirmation experiment of the buffy coat position, the position of the upper surface of the top board of the stopper 11 was adjusted to be the 5 mL-scale position of the container 21 by the screw mechanism of the stopper 11 and the adapter 12. Then, a porous ceramic material comprised of hydroxyapatite (porosity 75%, average cross-sectional area of pores $18.6 \times 10^{-3}$ mm$^2$, cylindrical shape with diameter: 11 mm, height 10 mm, containing pores arrayed in one direction (height direction of the material) was placed on the top board of the stopper 11 such that the arrayed direction of the pores was perpendicular to the top board. The container 21 was filled with rabbit heart blood to the 8 mL scale of the container 21. At this point, the blood rapidly penetrated into the porous ceramic material due to the capillary action. Thereafter, the blood was centrifuged at 4° C. and 1500×g for 10 min.

Comparative Example 1

Using a container same as the container 21 used in Example 1 and a porous ceramic material same as that used in Example 1, and without using stopper 11 and adapter 12, the porous ceramic material was set on the inside bottom of the container 21, rabbit heart blood was filled in the container 21 up to the 8 mL scale and the container was left standing for 10 min to allow the rabbit heart blood to penetrate into the porous ceramic material.

Comparative Example 2

Using a container, a stopper and an adapter same as the container 21, stopper 11 and adapter 12 used in Example 1, the position of the upper surface of the top board of the stopper 11 was adjusted to be the 5 mL-scale position of the container 21 by the screw mechanism of the stopper 11 and the adapter 12. Then, a porous ceramic material comprised of hydroxyapatite (porosity 55%, average cross-sectional area of pores $43.2 \times 10^{-3}$ mm$^2$, cylindrical shape with diameter: 11 mm, height 10 mm, having a three-dimensional net pore structure (no communication between pores) was placed on the top board of the stopper 11. The container 21 was filled with rabbit heart blood to the 8 mL scale of the container 21. At this point, penetration of blood into the porous ceramic material due to the capillary action was not observed. Thereafter, the blood was centrifuged at 4° C. and 1500×g for 10 min.

Figure 5:
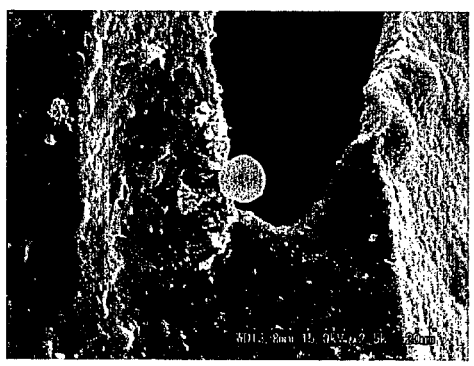
FIG. 5 shows SEM-observed images of the cross section of the material produced in the Example.
Figure 5:
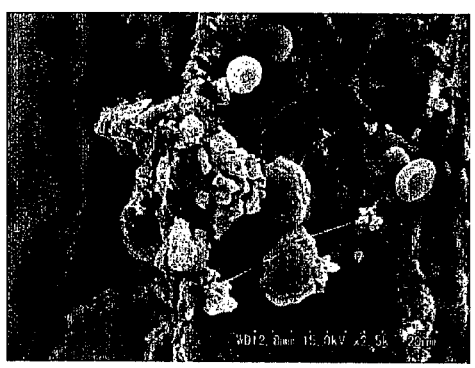

FIG. 5 shows SEM-observed images of the cross section of the material prepared in Example 1. FIG. 5(A) is an observation image of the upper part and FIG. 5(B) is an observation image of the lower part. In FIG. 5(A) showing the upper part scarcely contains the cells, whereas the presence of the nucleated cells can be confirmed in FIG. 5(B) showing the lower part. In both FIG. 5(A) and FIG. 5(B), erythrocytes unnecessary for tissue regeneration are small in number.

Figure 6:
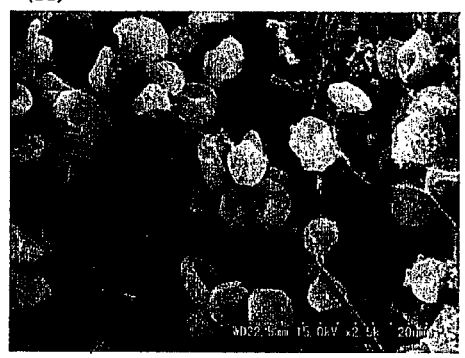
FIG. 6 shows SEM-observed images of the cross section of the material produced in Comparative Example 1.
Figure 6:

FIG. 6 shows SEM-observed images of the cross section of the material prepared in Comparative Example 1. FIG. 6(A) is an observation image of the upper part and FIG. 6(B) is an observation image of the lower part. In FIG. 6(A) showing the upper part and FIG. 6(B) showing the lower part, many cells can be confirmed, though most of them are erythrocytes unnecessary for tissue regeneration.

A comparison of Example 1 and Comparative Example 1 reveals that the method of the present invention eliminates erythrocytes, concentrates cells useful for tissue repair and adheres them to porous ceramics.

Figure 7:
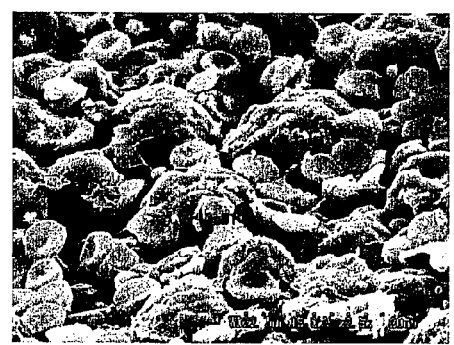
FIG. 7 shows SEM-observed images of the cross section of the material produced in Comparative Example 2.
Figure 7:

FIG. 7 shows SEM-observed images of the cross section of the material prepared in Comparative Example 2. FIG. 7(A) is an observation image of the upper part and FIG. 7(B) is an observation image of the lower part. While both upper and lower parts mainly contain erythrocytes unnecessary for tissue regeneration, which entered the inside by the centrifugation operation, the number thereof is higher in FIG. 8(A) showing the upper part than in FIG. 8(B) showing the lower part.

INDUSTRIAL APPLICABILITY

The present invention provides a production method of an implant material, which simultaneously achieves, without using an additive such as medicament and the like, a high repair effect of bone tissue and cartilage tissue and convenience of preparation, particularly in the regeneration of bone defects or cartilage defects, in the orthopedic field.

This application is based on a patent application No. 2010-262538 filed in Japan, the contents of which are incorporated in full herein.

EXPLANATION OF SYMBOLS 1 top board
2 through hole
10 porous ceramic material positioning means
11 stopper
12 adapter
12a upper end of adapter
21 container
22 porous ceramic material
22a pores
31 erythrocyte layer
32 buffy coat layer
33 serum layer

The invention claimed is:

1. A method of producing an implant material, the method comprising
   (A): setting a porous ceramic material having substantially unidirectionally arrayed pores at any depth position inside a container, wherein the porous ceramic material is a porous calcium phosphate-based ceramic material, (B): filling the container with a cell-comprising liquid comprising bone marrow blood, peripheral blood, or both, wherein the cell in the cell-comprising liquid is not collected and cultivated from said bone marrow blood, peripheral blood, or both in advance of said filling, and (C): applying, to the container, a centrifugal force in a direction along an axis of the container, wherein the centrifugal force is 100×g to 2000×g in (C), wherein the cell-comprising liquid forms a buffy coat layer formed in (C), wherein, in (A), a porous ceramic material positioning means having through holes permitting the cells in the cell-comprising liquid to pass through, which is for setting the porous ceramic material at any depth position inside the container is used together with the container, wherein the porous ceramic material positioning means includes a stopper which is a tube having a top board formed with plural through holes permitting the cells to pass through and an adapter which is a member for adjusting the height position of the top board of the stopper in conjunction with the stopper, wherein a surface of the top board of the stopper is a surface on which the porous ceramic material is placed, wherein the plural through holes in the top board are plural through holes having a circular cross section with the pore size (diameter) of not more than 0.5 mm and not less than 6 mm, and wherein, in (A), the porous ceramic material is set such that a long axis of the substantially unidirectionally arrayed pores is along the axis of the container, and is set such that at least a part thereof comes into contact with the buffy coat layer produced formed in (C).

2. The method of claim 1, wherein the cell-comprising liquid comprises bone marrow blood.

3. The method of claim 1, wherein the cell-comprising liquid comprises peripheral blood.

4. The method of claim 1, wherein the cell-comprising liquid comprises bone marrow blood and peripheral blood.

* * * * *